United States Patent [19]
Fujikura et al.

[11] Patent Number: 4,585,893
[45] Date of Patent: Apr. 29, 1986

[54] PROCESS FOR PRODUCING 4-HOMOISOTWISTANE-3-CARBOXYLIC ACID

[75] Inventors: Yoshiaki Fujikura, Ichikaimachi; Naotake Takaishi; Yoshiaki Inamoto, both of Utsunomiya, all of Japan

[73] Assignee: KAO Corporation, Tokyo, Japan

[21] Appl. No.: 514,847

[22] Filed: Jul. 18, 1983

[30] Foreign Application Priority Data

Jul. 22, 1982 [JP] Japan .................................. 57-128234

[51] Int. Cl.$^4$ ............................................. C07C 61/12
[52] U.S. Cl. .................................................. 562/499
[58] Field of Search ......................................... 562/499

[56] References Cited

U.S. PATENT DOCUMENTS 4,002,674  1/1977  Inamoto et al. ...................... 562/499
4,002,690  1/1977  Inamoto et al. ...................... 562/499
4,070,540  1/1978  Inamoto et al. ...................... 562/499

FOREIGN PATENT DOCUMENTS 0073847  6/1977  Japan .................................. 562/499

OTHER PUBLICATIONS

Inorganic Synthesis, vol. 2, 1946, pp. 81–85; Gilliland et al.
Chemical Abstracts, vol. 87, Abstract No. 117638b (1977).
Chemical Abstracts, vol. 87, Abstract No. 52882e (1977).
Chemical Abstracts, vol. 84, Abstract No. 179769s (1976).
N. Takaishi et al., "Functionalizations and Bridgehead Reactivity of 4–Homoisotwistane (Tricyclo [5,3,1,0$^{3,8}$]Undecane), Synthesis of 3–Substituted Derivatives", Journal of the Chem. Society, Chem. Communications, No. 10, May 21, 1975, pp. 371–372.
The Merck Index, 1976, 1819, Carbon Monoxide, pp. 231–232.

Primary Examiner—Natalie Trousof
Assistant Examiner—Patricia M. Scott
Attorney, Agent, or Firm—Oblon, Fisher, Spivak, McClelland & Maier

[57] ABSTRACT

An industrially advantageous process for producing 4-homoisotwistane-3-carboxylic acid.

According to the invention, tricyclo[5.2.1.0$^{2,6}$]dec-8-yl-methylformate (II) is contacted with an inorganic strongly acidic catalyst to obtain 4-homoisotwistane-3-carboxylic acid (I).

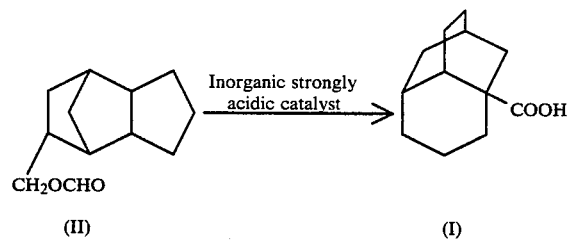

6 Claims, No Drawings

PROCESS FOR PRODUCING 4-HOMOISOTWISTANE-3-CARBOXYLIC ACID

BACKGROUND OF THE INVENTION

1. Field of the Invention

This invention relates to a process for producing 4-homoisotwistane-3-carboxylic acid which belongs to tricyclo carboxylic acids.

2. Description of the Prior Art 4-homoisotwistane-3-carboxylic acid is a known compound found by the present inventors (refer to Japanese Patent Publication No. 20979/1978) and esters of 4-homoisotwistane-3-carboxylic acid derived therefrom are compounds which are known to have antivirus activity (refer to Japanese Patent Publication No. 8494/1980).

Heretofore, the 4-homoisotwistane-3-carboxylic acid (I) has been synthesized by way of a very much troublesome synthesizing process as shown by the following schemes (yield from the starting material: 15%). However, cyclohexadiene as the starting material can not be obtained industrially inexpensively now, and this synthetic process has been very much inconveninent.

(Conventional Method 1)

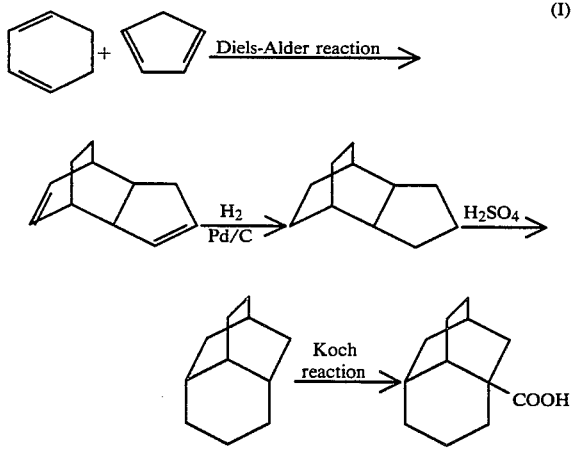

In view of the above, the inventors of the present application have previously found a process for synthesizing 4-homoisotwistane-3-carboxylic acid, said process comprising reacting 8-hydroxy-methyl-tricyclo [5.2.1.0$^{2,6}$]decane, which can be synthesized from industrially available dicyclopentadiene, with carbon monoxide and water, or with formic acid in the presence of sulfuric acid thereby transforming the skelton thereof while carboxylating the 3-position of the 4-homoisotwistane simultaneously, and filed a patent application (Japanese Patent Application No. 8814/1981). However, as shown in the following schemes, the reaction proceeds through a multistep of skelton transformation and, therefore, the intermediates are liable to be subjected to side reactions and the yield has actually been as low as about 20%.

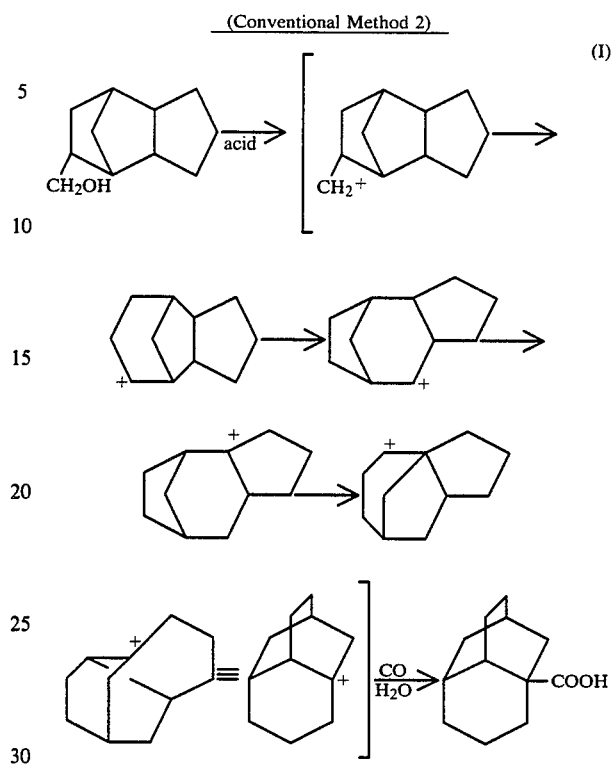

Such conventional carboxylating reactions are generally referred to as Koch reactions, which have the following defects inherent to the Koch reactions.

Among the Koch reactions, a CO pressure method of reacting an alcohol or olefin with carbon monoxide and water in the presence of an inorganic strongly acidic catalyst, involves the following drawbacks; (1) since it is important to increase the pressure of carbon monoxide (CO) for suppressing the formation of tars in order to improve the yield, it is required to use a pressure-proof vessel, which means a restriction in view of the facility; (2) it requires energy for pressurizing the carbon mono-oxide; and (3) since the reaction is carried out in the presence of a water-containing acid catalyst, special materials are required for the autoclave, which causes an increase in the installation cost. Among the Koch reactions, a formic acid method of reacting an alcohol or olefin with formic acid in the presence of an inorganic strongly acidic catalyst, although being free from the drawbacks as in the CO pressure method since the reaction can be taken place under ambient pressure, involves several drawbacks in that (1) the yield will be decreased unless formic acid is used in a large excess to the alcohol or olefin; (2) the excess formic acid in the reaction system is decomposed by the acid into water and carbon monoxide, with the resulting water reducing the catalyst activity, and the carbon monoxide being discharged as a gas to cause undesired circumstantial problems; (3) since the excess formic acid can not be recovered, it results in disadvantages in view of the cost; and (4) since formic acid is often less miscible with olefins and alcohols, it requires to introduce the formic acid and the reaction substrate at an accurate dropping rate to the reaction system for preventing the decrease in the yield, which renders the procedures much complicated.

Further, one of the common problems to those processes is that acid has to be used in an extremely large amount. If the acid can not be recovered, the disposition for the great amount of wasted acid causes a significant problem in view of the production step. Even if the acid can be recovered, the use of such great amount of acid inevitably leads to the disadvantage of decreasing the charge amount per one reaction cycle.

As described above, the conventional process for producing 4-homoisotwistane-3-carboxylic acid has involved a variety of problems both in the yield and the reaction process and has not yet been completely satisfactory.

SUMMARY OF THE INVENTION

In view of the foregoing present status, the inventors of the present application have made an earnest study for the advantageous process for producing 4-homoisotwistane-3-carboxylic acid and, as a result, have accomplished this invention on the basis of the discovery that the 4-homoisotwistane-3-carboxylic acid (I) can be obtained while eliminating the defects in the prior art process, with much convenience and at a good yield by contacting the formate (II) as the starting material with an inorganic strongly acidic catalyst in accordance with the following scheme:

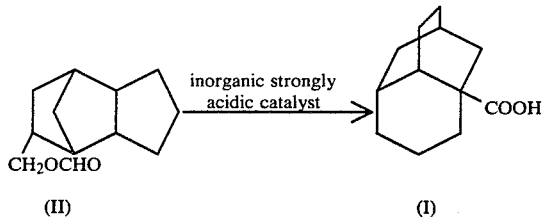

Specifically, this invention relates to a process for producing 4-homoisotwistane-3-carboxylic acid (I), wherein tricyclo[5.2.1.0$^{2,6}$]dec-8-yl-methylformate (II) is contacted with an inorganic strongly acidic catalyst thereby transforming the skeleton while carboxylating the 3-position of 4-homoisotwistane simultaneously.

DETAILED DESCRIPTION OF THE INVENTION AND PREFERRED EMBODIMENTS

The tricyclo[5.2.1.0$^{2,6}$]dec-8-yl-methylformate (II) as the starting material in this invention may have the formyloxymethyl group and 3, 4, 5-position trimethylene groups either at the exo- or endo-position and it can be produced by reacting a corresponding alcohol with formic acid in any one of known methods. That is, it may be produced either by reacting an alcohol with formic acid in admixture, or reacting the liquid mixture of them with a small amount of acid such as a concentrated sulfuric acid, aryl sulfonic acid and boron trifluoride-ether complex. Further, without limited only to these methods, any method can be utilized as the production process for the compound (II) so long as it gives esterification with formic acid.

The inorganic strong acid catalyst usable herein includes known catalysts employed in Koch reactions, for example, concentrated sulfuric acid (at a concentration higher than 80%), phosphoric acid, hydrofluoric acid, boron trifluoride-phosphoric acid, boron trifluoride hydrate, boron trifluoride-methanol, as well as mixtures thereof. In the process according to this invention, the reaction occurs even with the use of a small amount of the acid catalyst, and an increase in the amount of the acid leads to the improvement in the yield. Accordingly, the amount of the inorganic strongly acidic catalyst employed, while varying depending on the type of the catalyst, is preferable between 0.5-24 mols per one mol of the formic acid ester (I) as the starting material in the case, for example, of concentrated sulfuric acid (95%) and the amount is, preferably, less than 6 mol when taking the disposal of the wasted acid further into consideration.

The reaction temperature, while varying depending on the type of the acid catalyst, is preferably between 0°-80° C. If the reaction temperature is lower than 0° C., the reaction rate is very slow and the yield is reduced. While on the other hand, at a temperature higher than 80° C., the formation of tars is increased to provide economical disadvantages.

In the process according to this invention, while the reaction may be proceeded even in the absence of a reaction solvent, the reaction can also be taken place in the presence of such solvent as not interferring the reaction of this invention, for example, straight -alkanes such as n-pentane and n-hexane; or halogenated solvent such as carbon tetrachloride.

Although it is not usually required to pressurize the carbon monoxide, pressurization is effective in the case more improved reaction yield or more decreased amount of acid employed are desired. In such a case, since no substantial improvement can be expected with the pressure of the carbon monoxide up to about 5 atm, it is required to give pressure of more than 5 atm.

In the process according to this invention, it is not necessary to introduce carbon monoxide or formic acid separately, which simplifies the reaction procedures. Particularly, the amount of the acid used is only less than 1/7 as compared with the conventional process, the acid loss can be much decreased. Further, this is an extremely satisfactory process since the yield is as high as 63.9% (selectivity: 96%) as shown in Examples, irrespective of the multi-state skeleton transformation.

This invention will now be explained in more detail referring to the following examples.

EXAMPLE 1

Synthesis for 4-homoisotwistane-3-carboxylic acid:

To 588 g (6 mol) of 95% concentrated sulfuric acid at a temperature of 30° C., were added 194 g (1 mol) of tricyclo[5.2.1.0$^{2,6}$]dec-8-yl-methylformate under stirring for 2 hours (refer to literature, Japanese Patent Application Laid-Open No. 144354/1979). After the completion of the addition, they were continuously stirred at the same temperature for 30 min. After the reaction was over, they were poured into 460 g of ice and water and then extracted with chloroform. After washing the extract with saturated saline water, it was dried over anhydrous magnesium sulfate. After filtration, the solvent was distilled off and the residue was subjected to distillation to obtain 124 g of the above-mentioned carboxylic acid crude product (63.9% yield). Gas chromatography confirmed that purity of the produce was 96%. It was recrystallized from n-hexane to obtain purified product.

Melting point: 103°-105° C.

$^{13}$C-NMR (CDCl$_3$ solvent, TMS internal standard, $\delta_c(\ )$ represents multiplicity): 16.3 (t), 23.7 (t), 24.6 (d), 24.9 (t), 30.6 (t), 30.8 (d), 31.5 (t), 32.6 (t), 34.3 (d), 35.6 (t), 44.1 (s), 185.9 (s)

*$^{13}$C-NMR spectrum coincided with that of the standard sample.

Comparative Example 1

A mixture consisting of 450 g (4.6 mol) of 95% sulfuric acid and 100 ml of carbon tetrachloride was cooled in ice and water and kept at a temperature of 10°–15° C., into which was added dropwise over 2.5 hours a solution prepared by dissolving 16.6 g (0.10 mol) of 8-exo-hydroxymethyl-endo-tricyclo[5.2.1.0$^{2,6}$]decane in 55 g (1.20 mol) of 99% formic acid under stirring. After the completion of the addition, they were further stirred at the same temperature for 3 hours.

The reaction mixture was poured into 1 kg of crushed ice. After separating the aqueous phase, an aqueous phase was extracted with carbon tetrachloride, which was joined with separated organic phase and, after water washing, extracted three times with an aqueous 15% sodium hydroxide solution.

35% hydrochloric acid was dropped to this aqueous sodium hydroxide solution to adjust the pH to 1–2. After the extraction with ether, the ethereal phase was dried over anhydrous sodium sulfate and subjected to fractional distillation to obtain 3.88 g of crude 4-homo-isotwistane-3-carboxylic acid (20% yield) having boiling point at 135°–140° C./0.9 mmHg. When the product was purified through sublimation under a reduced pressure, both of the melting point and the spectroscopic properties of the purified product were identical with those of the standard 4-homoisotwistane-3-carboxylic acid sample (the standard sample was synthesized separately by the process as described by the present inventors in Japanese Patent Publication No. 20979/1978).

Reference Example 1

Synthesis for endo-tricyclo[5.2.1.0$^{2,6}$]deca-8-exo-yl-methylformate:

3.0 g of 8-exo-hydroxymethyl-endo-tricyclo [5.2.1.0$^{2,6}$]decane were dissolved into 30 ml of formic acid, into which was dropped 1 ml of concentrated sulfuric acid under stirring. After stirring at room temperature for 3 hours, they were diluted with incorporation of 100 ml of ethyl ether and then washed twice with water each time by 100 ml and further washed once with 100 ml of an aqueous 10% sodium carbonate solution. After drying the ether phase, it was concentrated and the residue was subjected to fractional distillation to obtain 3.0 g of the methylformate (86% yield).

Elementary analysis value (as $C_{12}H_{18}O_2$):
Calculated (%): C 74.19, H 9.34.
Found (%): C 74.43, H 9.20.
Boiling point: 116°–118° C./8 mmHg:
$\eta D^{20}$: 1.4964;
IR 1730 cm$^{-1}$, 1180 cm$^{-1}$.

What is claimed is:

1. A process for producing 4-homoisotwistane-3-carboxylic acid of the formula (I):

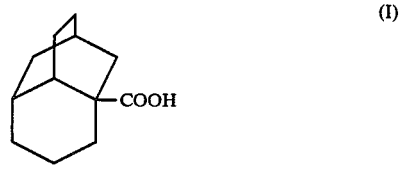

comprising:
(a) contacting tricyclo (5.2.1.0$^{2,6}$) dec-8-yl-methylformate of formula (II)

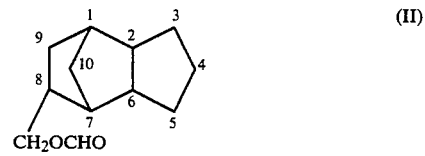

with about 0.5 to 24 mol of a strongly acidic inorganic catalyst per mol of the compound of formula (II).

2. The process of claim 1, wherein the strongly acidic inorganic catalyst is concentrated sulfuric acid.

3. The process of claim 1, wherein the strongly acidic inorganic catalyst is selected from the group consisting of concentrated sulfuric acid, phosphoric acid, hydrofluoric acid, boron trifluoride-phosphoric acid, boron trifluoride hydrate and boron trifluoride-methanol.

4. The process of claim 1, wherein carbon monoxide under pressure is used in a reaction system.

5. The process of claim 1 carried out at a temperature of between about 0° and 80° C.

6. The process of claim 1 carried out in the presence of a solvent selected from the group consisting of straight-chain alkanes and halogenated solvents.

* * * * *